United States Patent [19]

Taskovich

[11] Patent Number: 4,863,738

[45] Date of Patent: Sep. 5, 1989

[54] SKIN PERMEATION ENHANCER COMPOSITIONS USING GLYCEROL MONOOLEATE

[75] Inventor: Lina T. Taskovich, Palo Alto, Calif.

[73] Assignee: ALZA Corporation, Palo Alto, Calif.

[21] Appl. No.: 124,306

[22] Filed: Nov. 23, 1987

[51] Int. Cl.⁴ ............................................. A61F 13/00
[52] U.S. Cl. ...................................... 424/449; 424/484
[58] Field of Search .......................... 424/448, 449, 484

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,460,372 | 7/1984 | Campbell et al. | 604/897 |
| 4,568,343 | 2/1986 | Leeper et al. | 604/896 |
| 4,588,580 | 5/1986 | Gale et al. | 424/21 |
| 4,690,683 | 9/1987 | Chien et al. | 424/448 X |
| 4,746,515 | 5/1988 | Cheng et al. | 424/449 |

FOREIGN PATENT DOCUMENTS 10001949  8/1985  Fed. Rep. of Germany.

OTHER PUBLICATIONS

Idson B., "Percutaneous Absorption", Journal of Pharmaceutical Sciences, vol. 64, No. 6 (Jun. 1975), pp. 901-924.

Primary Examiner—Nancy A. B. Swisher
Attorney, Agent, or Firm—Shelley G. Precivale; Edward L. Mandell; Steven F. Stone

[57] ABSTRACT

A method for enhancing the flux of transdermally deliverable drugs through intact skin is described in which the drug is delivered simultaneously with glycerol monooleate. Preferred embodiments of therapeutic systems for delivering drug and glycerol monooleate employ matrix containing drug at a concentration above saturation.

17 Claims, 1 Drawing Sheet

SKIN PERMEATION ENHANCER COMPOSITIONS USING GLYCEROL MONOOLEATE

FIELD OF THE INVENTION

This invention relates to the transdermal delivery of drugs or other biologically active agents and more particularly to novel methods and compositions for enhancing the percutaneous absorption of drugs when incorporated in transdermal drug delivery systems.

RELATED PATENT APPLICATIONS

This invention is related to the inventions disclosed in copending, coassigned patent applications of Gale, et al for Transdermal Administration of Progesterone, Estradiol Esters and Mixtures Thereof, Ser. No. 07/019,162, now issued as U.S. Pat. No. 4,788,062; of Cheng, et al for Skin Permeation Enhancer Compositions Using Glycerol Monolaurate, Ser. No. 07/019,470, now issued as U.S. Pat. No. 4,746,515; and of Nedberge, et al for Transdermal Contraceptive Formulations, Ser. No. 07/019,163; all filed on Feb. 26, 1987.

BACKGROUND OF THE INVENTION

The transdermal route of parenteral delivery of drugs provides many advantages and transdermal systems for delivering a wide variety of drugs or other beneficial agents are described in U.S. Pat. Nos. 3,598,122, 3,598,123, 4,379,454, 4,286,592, 4,314,557 and 4,568,343 for example, all of which are incorporated herein by reference. In many cases, drugs which would appear to be ideal candidates for transdermal delivery are found to have such low permeability through intact skin that they cannot be delivered at therapeutically effective rates from reasonably sized systems.

In an effort to increase skin permeability so that drugs can be delivered at therapeutically effective rates, it has been proposed to pretreat the skin with various chemicals or to concurrently deliver the drug in the presence of a permeation enhancer. Various materials have been suggested for this purpose as described in U.S. Pat. Nos. 4,299,826, 4,343,798, 4,046,886, 4,130,643, 4,405,616, 4,335,115, 4,130,667, 3,903,256, 4,379,454, 3,527,864, 3,952,099, 3,896,238, 3,472,931 which are incorporated herein by reference, British Pat. No. 1,001,949 and Idson, Percutaneous Absorption, J. Phar. Sci., Vol. 64, No. b6, June 1975, pp. 901-924 (particularly 919-921).

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5-50 cm$^2$), is at therapeutic levels. Additionally, the enhancer, when applied to the skin surface from a controlled drug delivery system, should be non-toxic, non-irritating on prolonged exposure and under occlusion, and non-sensitizing on repeated exposure. Preferably it should also be odorless and capable of delivering drugs without producing burning or tingling sensations.

It is often difficult to predict which enhancers will work for which drugs. In systemic drug delivery applications, a compound that enhances the permeability of one drug or a family of drugs may not necessarily enhance the permeability of another. Therefore, the usefulness of a particular compound must be analyzed on a drug by drug basis.

According to our invention, we have discovered that glycerol monooleate (GMO), is effective in enhancing the permeation of steroids, nitrates and biperiden, through body surfaces and membranes generally, and through skin in particular, and when formulated in pharmaceutical compositions with other materials appears to satisfy the criteria noted above. Most importantly, glycerol monooleate is able to enhance the permeability of these drugs such that therapeutic delivery rates can be attained with reasonably sized systems.

It is accordingly an object of our invention to increase the permeability of body surfaces of animals and humans, including the mucosa and other membranes and more particularly of human skin, for the systemic delivery of particular drugs by the concurrent application of the drug and GMO to the body surface.

It is another object of our invention to provide examples of compositions of matter for application to the skin which comprise GMO and one or more drugs, specifically steroids, alone or in combinations, nitrates or biperiden.

These and other objects and advantages will be readily apparent from the following description with reference to the accompanying drawings wherein a composition of matter is applied to a body surface or membrane to deliver at least one drug, at a therapeutically effective rate, by permeation through a body surface or membrane comprising, in combination: at least one drug selected from the group consisting of steroids, nitrates and biperiden and a permeation enhancing amount of glycerol monooleate.

DESCRIPTION OF THE INVENTION

Figure 1:
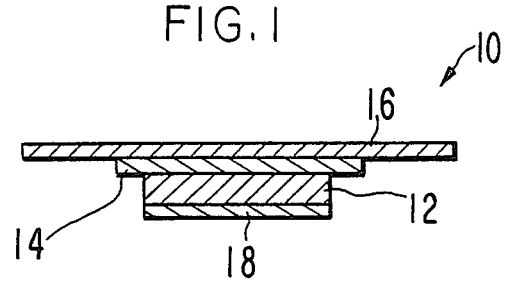
FIG. 1 is a cross-sectional view of one embodiment of the transdermal therapeutic system according to this invention.

According to our invention we have discovered that GMO can be used to enhance the permeability of select drugs through body surfaces. Specifically, we have shown that GMO enhances the permeability such that therapeutic delivery rates can be attained for steroids, such as progesterone, estradiol, ethinyl estradiol, levonorgestrel, nitrates such as nitroglycerin and isosorbide dinitrate and biperiden. Some drugs can permeate the skin at therapeutically effective rates, without any assistance. One such drug is nitroglycerin. However, some delivery systems require that nitroglycerin be delivered at high fluxes. The use of GMO, as taught by this invention, will help attain the desired high flux. It is anticipated that glycerol monooleate will also act as a permeation enhancer for other steroids in the following classes: estrogens and estrogen esters, progestogens and progestogen esters, androgens such as testosterone, adrenal corticoids and adrenal corticoid esters such as hydrocortisone.

According to our invention GMO and the drug to be delivered are placed in drug and GMO transmitting relationship to the appropriate body surface, preferably in a carrier therefor, and maintained in place for the desired period of time. The drug and GMO are typically dispersed within a physiologically compatible matrix or carrier as more fully described below which may be applied directly to the body as an ointment, gel, cream, suppository or sublingual or buccal tablet for example, but are more preferably administered from a transdermal therapeutic system as more fully described below.

As used herein the term "transdermal" delivery relates to the delivery of a drug by passage through intact skin into the vascular system below the epidermis for transport by the blood stream. Thus transdermal delivery is distinguished from topical application to the surface of intact skin for topical treatment or to application to open wounds or to skin lacking the stratum corneum such as burned or abraded skin.

We have also found that GMO, in addition to its known low toxicity and colorless and odorless nature, does not sensitize skin on repeated exposure. Further, it can be applied to the skin in compositions that do not produce irritation even on occlusion and repeated application to the same site and is capable of enhancing drug flux without producing objectionable skin sensations. GMO is especially suited for incorporation into monoliths or bilaminates containing from about 1-20% GMO and about 2-20% drug.

GMO has a permeation enhancing effect on the transport of steroids, nitrates and biperiden through body surface tissues generally in addition to the skin. Nevertheless, because skin is one of the most effective body barriers to permeation of foreign substances, the effect of GMO on skin permeation makes it extremely useful in transdermal delivery. The following description of preferred embodiments of the invention is therefore directed primarily to improving systemic delivery of these drugs.

Referring now to FIG. 1, a transdermal therapeutic system 10 according to this invention is shown which comprises a drug/permeation enhancer reservoir 12 in the form of a matrix containing one or more drugs and GMO. The reservoir 12 is covered by an impermeable backing 14 which is preferably sized slightly larger in circumference than reservoir 12. Means 16 for maintaining the system on the skin, may either be fabricated together with or provided separately from the remaining elements of the system which means in the embodiment of FIG. 1 takes the form of an adhesive overlay. The use of an adhesive overlay with this invention is preferred to the use of an in-line adhesive applied to the skin proximal surface of reservoir 12 because GMO may adversely affect the adhesive properties of some pharmaceutically acceptable contact adhesives. For this reason, impermeable backing layer 14 is preferably sized slightly larger than the reservoir 12 to provide a peripheral area around reservoir 12 free of GMO to prevent adverse interaction between the adhesive in the overlay 16 and any of the GMO which may seep from under the base of reservoir 12 during use. A strippable release liner 18, adapted to be removed prior to application would normally be included in the packaged product.

Various materials suited for the fabrication of the various layers are disclosed in the aforementioned patents. The composition of the matrix may be either an aqueous or anhydrous base. Suitable matrices or carriers are described in the above identified patents, for example, gelled or thickened mineral oil, petroleum jelly and various aqueous gels and hydrophilic polymers. Suitable matrix materials also include, without limitation, natural and synthetic rubbers such as polybutylene, polyisobutylene, polybutadiene, polyethylene, styrenebutadiene, copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinylacetate (EVA) polymers described in U.S. Pat. No. 4,144,317 (which is incorporated herein by reference). Typically the drug is dispersed through the matrix or carrier at a concentration in excess of saturation, the amount of the excess being a function of the intended useful life of the system. The drug however, may be present at initial levels below saturation without departing from this invention. The GMO is preferably dispersed through the matrix at a concentration sufficient to provide permeation enhancing concentrations of GMO in the reservoir throughout the anticipated administration time.

In addition to the drug and GMO, which are essential to the invention, the matrix may also contain other materials such as dyes, pigments, inert fillers or other permeation enhancers, excipients, and conventional components of pharmaceutical products or transdermal therapeutic systems as known to the art.

Figure 2:
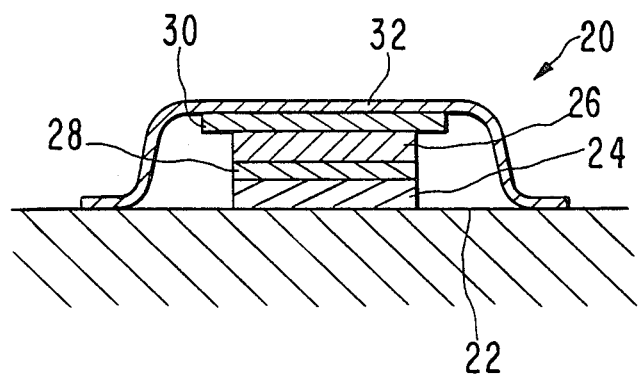
FIG. 2 is cross-sectional view of another embodiment of the transdermal therapeutic system according to this invention.

Referring now to FIG. 2 another embodiment of this invention, system 20, is shown in place upon the skin 22 of a patient. This embodiment is a multilaminate transdermal therapeutic system. System 20 consists of a drug reservoir 24 and a GMO reservoir 26 which is preferably made from substantially the same matrix as used to form reservoir 24 and which is substantially free of any undissolved drug. A rate controlling membrane 28 for controlling the release rate of GMO from reservoir 26 to the skin may also be utilized between the GMO reservoir 26 and the drug reservoir 24, if desired. Suitable rate controlling membranes may be fabricated from permeable, impermeable or microporous materials as are known in the art to control the rate of agents or fluids into and out of delivery devices. Suitable materials include, without limitation, polyvinylacetate and ethylene vinylacetate.

The rate controlling membrane 28 may be permeable to the passage of drug and in that instance, the system will be at equilibrium with some drug present in the GMO reservoir 26 and some GMO present in the drug reservoir 24. Alternately, the rate controlling membrane 28 may be substantially impermeable to the passage of drug and in that instance, while the GMO may be in equilibrium in both reservoirs, the GMO reservoir will be substantially free of any drug.

An advantage of the system described in FIG. 2 is that the drug loaded reservoir 24 is concentrated at the skin surface rather than throughout the entire mass of the reservoir. This functions to reduce the amount of drug in the system while maintaining an adequate GMO supply.

Superimposed over the enhancer reservoir 26 is an impermeable backing 30 and adhesive overlay 32 as described above with respect to FIG. 1. In addition, a strippable release liner (not shown) would be provided on the system prior to use as described with respect to FIG. 1 and removed prior to application to the skin 22.

In the embodiments of FIGS. 1 and 2, the carrier or matrix material has sufficient viscosity to maintain its shape without oozing or flowing. If the matrix or carrier is a low viscosity flowable material, the composition can be fully enclosed in a pouch or pocket between the impermeable backing and a permeable or microporous skin contacting membrane as known to the art from U.S. Pat. No. 4,379,454, noted above, for example. Although the invention is most useful with drugs whose permeability is too low for therapeutic effects to be obtained in the absence of an enhancer, its use with systems employing drug rate controlling membranes such as are disclosed in U.S. Pat. No. 3,598,122 and 3,598,123 noted above and to obtain high drug fluxes, is also contemplated.

EXAMPLE I

A transdermal therapeutic system as described with respect to FIG. 1 for administration of progesterone was formulated from 5.0% progesterone, 20.0% GMO, 40.5% EVA 46 and 34.5 Staybelite Ester #5 (Hercules, Inc.).

The following table provides in vitro progesterone skin flux data for various formulations. Comparisons are made with two other permeation enhancers: sucrose recinoleate (SR) and sucrose monolaurate (SML).

TABLE I

| FORMULATION, weight percent | PROGESTERONE SKIN FLUX, $\mu g/cm^2 hr$ |
| --- | --- |
| 25.0% GMO, 10.0% Progesterone, 36.0% EVA 40, 29.0% Staybelite Ester #5 | 2.38 |
| 2.5% Progesterone, 97.5% EVA 51 | 0.14 |
| 25.5% SR, 8.0% Progesterone, 39.1% EVA 40, 27.4% Staybelite Ester #5 | 1.01 |
| 25.5% SML, 10.0% Progesterone, 35.8% EVA 40, 28.7% Staybelite Ester #5 | 2.33 |
| 25.4% PEG 40 Castor Oil, 8.0% Progesterone 39.1% EVA 40, 27.5% Staybelite Ester #5 | 0.75 |

Table II provides comparisons of the in vitro skin flux ($\mu g/cm^2 hr$) of estradiol and progesterone across human cadaver skin, with and without the presence of glycerol monooleate.

TABLE II

| CONCENTRATION mg/g | SOLUBILITY mg/g | VEHICLE wt % | TEMPERATURE degrees C. | FLUX $\mu g/cm^2/hr$ |
| --- | --- | --- | --- | --- |
| Estradiol | | | | |
| 20 | 0.45 | 10% GMO in MO | 32 | 0.30 |
| 20 | 0.003 | MO (control) | 32 | 0.07 |
| Progesterone | | | | |
| 14.0 | 8.62 | 10% GMO in MO | 32 | 0.83 |
| 5.8 | 4.65 | MO (control) | 32 | 0.26 |
| 14.0 | 11.18 | 10% GMO in MO | 37 | 1.65 |
| 5.8 | 5.79 | MO (control) | 37 | 0.44 |
| 20 wt % | — | 5% GMO in PIB/MO | 32 | 1.6 |
| 20 wt % | — | PIB/MO | 32 | 0.8 |

EXAMPLE II

Comparative data was obtained on two prototype transdermal systems according to this invention. Measurements were taken to ascertain the maximum estradiol levels following a 24 hour application of an ethinyl estradiol containing system, on male subjects. The systems were comprised of 40% or 46% vinylacetate content EVA (EVA 40 or EVA 46); glycerol monooleate (GMO) or polyethylene glycol monolaurate (PEGML); Staybelite Ester #5 tackifier; and ethinyl estradiol. The prototype of this invention was comprised of (by weight percent): 40.5% EVA 46, 20% GMO, 34.5% Staybelite Ester #5 and 5% ethinyl estradiol. The estradiol concentration measured after 24 hours was 42 pg/ml. For comparison, a prototype was made comprised of (by weight percent): 40.6% EVA 40, 25% PEGML, 28.4% Staybelite Ester #5 and 6% ethinyl estradiol. The estradiol concentration, measured by the same methods as that for the GMO containing prototype, was 16 pg/ml.

This invention also contemplates delivery of a steroid mixture. This is illustrated by the following example.

EXAMPLE III

A transdermal therapeutic system as described with respect to FIG. 1 for the administration of ethinyl estradiol and levonorgestrel was formulated from: 5 wt % levonorgestrel, 0.5 wt % ethinyl estradiol, 37.8 wt % EVA 40, 26.6 wt % Staybelite Ester #5 and 30.1 wt % GMO. The in vitro skin flux was measured over a seven day period, at 37° C. The following table shows the flux data averaged for thirteen samples for both drugs and GMO:

TABLE III

| DAY | FLUX, $\mu g/cm^2/hr$ | | | | | | |
| --- | --- | --- | --- | --- | --- | --- | --- |
| | 1 | 2 | 3 | 4 | 5 | 6 | 7 |
| Ethinyl estradiol | 0.137 | 0.181 | 0.194 | 0.204 | 0.160 | 0.174 | 0.165 |
| Levonorgestrel | 0.125 | 0.166 | 0.170 | 0.190 | 0.191 | 0.211 | 0.211 |
| GMO | 101.9 | 5.4 | 4.6 | 4.0 | 4.6 | 6.9 | 9.5 |

Table IV provides comparisons of the in vitro skin flux ($\mu g/cm^2 hr$) of nitroglycerin isosorbide dinitrate and biperiden across human cadaver skin, with and without the presence of glycerol monooleate. The vehicles used were silicone, polyisobutylene/mineral oil (PIB/MO) and isopropyl lauolate (IPL).

TABLE IV

| CONCENTRATION, weight % | VEHICLE wt % | TEMPERATURE, degrees C. | FLUX, $\mu g/cm^2/hr$ |
| --- | --- | --- | --- |
| Nitroglycerin | | | |
| 4 wt % | 7% GMO in silicone | 32 | 21 |
| 4 wt % | Silicone (control) | 32 | 12 |
| 4 wt % | 3% GMO + 9% IPL in PIB/MO | 32 | 28.2 |
| 4 wt % | 12% IPL in PIB/MO (control) | 32 | 22.2 |
| 4 wt % | 6% GMO in PIB/MO | 32 | 21.0 |
| 4 wt % Isosorbide Dinitrate | PIB/MO (control) | 32 | 11.3 |

TABLE IV-continued

| CONCENTRATION, weight % | VEHICLE wt % | TEMPERATURE, degrees C. | FLUX, μg/cm²/hr |
|---|---|---|---|
| 4 wt % | 5% GMO in PIB/MO | 32 | 16.6 |
| 4 wt % | PIB/MO (control) | 32 | 10.5 |
| 5 wt % | 3.75% GMO in PIB/MO | 32 | 11.1 |
| 5 wt % | PIB/MO (control) | 32 | 8.2 |
| Biperiden | | | |
| 2 wt % | 10% GMO in MO | 32 | 40.5 |
| 2 wt % | MO (control) | 32 | 14.5 |

Having thus generally described our invention and having provided specific embodiments thereof it will be readily apparent to workers skilled in the art that various modifications and substitutions can be made without departing from the scope of this invention which is limited only to the following claims.

We claim:

1. A composition of matter for application to a body surface or membrane to deliver at least one drug, at a therapeutically effective rate, by permeation through a body surface or membrane comprising, in combination: at least one drug selected from the group consisting of steroids, nitrates and biperiden and a permeation enhancing amount of glycerol monooleate.

2. The composition of claim 1 further comprising a carrier having said drug and glycerol monooleate dispersed throughout.

3. The composition of claim 2 wherein said drug is present in an amount in excess of its saturation concentration in the carrier.

4. The composition of claims 1 wherein said body surface or membrane is intact skin.

5. The composition of claim 1 wherein said steroid is selected from the group consisting of estrogens, estrogen esters, progestogens, progestogen esters, androgens, adrenal corticoids and adrenal corticoid esters.

6. The composition of claim 1 wherein said nitrate is selected from the group consisting of nitroglycerin and isosorbide dinitrate.

7. A transdermal therapeutic system comprising a composition of matter for application to a body surface or membrane comprising at least one drug selected from the group consisting of steroids, nitrates and biperiden and a permeation enhancing amount of glycerol monooleate, in combination with:

an occlusive backing behind the skin distal surface of said composition; and means for maintaining said composition in drug and glycerol monooleate transferring relationship to intact skin.

8. The system of claim 7 wherein said drug and glycerol monooleate are contained within a single reservoir means.

9. The system of claim 7 wherein said drug and glycerol monooleate are contained within separate reservoir means.

10. The system of claim 7 wherein said steroid is selected from the group consisting of progesterone, estradiol valerate, estradiol, ethinyl estradiol and levonorgestrel.

11. The system of claim 7 wherein said nitrate is selected from the group consisting of nitroglycerin and isosorbide dinitrate.

12. The system of claim 7 wherein said drug is present at a concentration sufficient to maintain the concentration above saturation for an extended period of time and said glycerol monooleate is present at a concentration sufficient to provide permeation enhancement throughout said extended period of time.

13. A method for enhancing the flux of at least one drug selected from the group consisting of steroids, nitrates and biperiden through a body surface or membrane which comprises placing a drug source in drug transmitting relationship to said surface or membrane in the presence of a permeation enhancing amount of glycerol monooleate.

14. The method of claim 13 wherein the drug source contains drug in excess of its saturation concentration in said source.

15. The method of claim 13 wherein said body surface or membrane is intact skin.

16. The method of claim 13 wherein said steroid is selected from the group consisting of progesterone, estradiol valerate, estradiol, ethinyl estradiol and levonorgestrel.

17. The method of claim 13 wherein said nitrate is selected from the group consisting of nitroglycerin and isosorbide dinitrate.

* * * * *